United States Patent
Garrec et al.

(10) Patent No.: US 9,744,064 B2
(45) Date of Patent: Aug. 29, 2017

(54) LOWER EXOSKELETON

(71) Applicants: Philippe Garrec, Gif sur Yvette (FR); Flavien Coste, Champvoisy (FR); Serge Grygorowicz, Gy l'Eveque (FR); Yann Perrot, Sainte-Genevieve des Bois (FR); Dominique Ponsort, Bievres (FR); Aurelie Riglet, Dammarie sur Loing (FR)

(72) Inventors: Philippe Garrec, Gif sur Yvette (FR); Flavien Coste, Champvoisy (FR); Serge Grygorowicz, Gy l'Eveque (FR); Yann Perrot, Sainte-Genevieve des Bois (FR); Dominique Ponsort, Bievres (FR); Aurelie Riglet, Dammarie sur Loing (FR)

(73) Assignees: COMMISSARIAT A L'ENERGIE ATOMIGUE ET AUX ENERGIES ALTERNATIVES, Paris (FR); ROBOTIQUES 3 DIMENSIONS, Auxerre (FR)

( * ) Notice: Subject to any disclaimer, the term of this patent is extended or adjusted under 35 U.S.C. 154(b) by 440 days.

(21) Appl. No.: 14/352,200

(22) PCT Filed: Oct. 12, 2012

(86) PCT No.: PCT/EP2012/070333
§ 371 (c)(1),
(2) Date: Apr. 16, 2014

(87) PCT Pub. No.: WO2013/057057
PCT Pub. Date: Apr. 25, 2013

(65) Prior Publication Data
US 2014/0257160 A1  Sep. 11, 2014

(30) Foreign Application Priority Data
Oct. 17, 2011  (FR) ........................... 11 59359

(51) Int. Cl.
*A61F 5/00* (2006.01)
*A61F 5/01* (2006.01)
(Continued)

(52) U.S. Cl.
CPC ......... *A61F 5/0102* (2013.01); *A61H 1/0255* (2013.01); *A61H 3/00* (2013.01);
(Continued)

(58) Field of Classification Search
CPC ....... A61F 5/0102; A61H 3/00; A61H 1/0255; A61H 2201/163; A61H 2201/165;
(Continued)

(56) References Cited

U.S. PATENT DOCUMENTS 7,628,766 B1 * 12/2009 Kazerooni ............... A61F 5/00
601/35
2006/0064047 A1    3/2006 Shimada et al.
(Continued)

FOREIGN PATENT DOCUMENTS

GB    2 260 495 A    4/1993

OTHER PUBLICATIONS

International Search Report for PCT/EP2012/070333 dated Mar. 1, 2013.

*Primary Examiner* — Quang D Thanh
(74) *Attorney, Agent, or Firm* — Sughrue Mion, PLLC

(57) ABSTRACT

A lower exoskeleton for a user including a pelvic element (1) with a mechanism for securing to an upper part of the user's body; two lower supports (2) with a mechanism for securing to the user's lower limbs and which rest on the ground during stance phases, each of the supports having a thigh segment and a tibia segment connected by a knee link to allow flexion and extension; and hip links for connecting the two lower supports to the pelvic element. The pelvic element has a an inner segment (30) extending symmetrically in
(Continued)

relation to a central sagittal plane; and two outer segments (33) extending symmetrically and connected to respective distal ends of the inner segment by linking members (31, 32, 34; 31'), allowing flexion between the inner segment and each outer segment along two orthogonal axes.

8 Claims, 2 Drawing Sheets

(51) Int. Cl.
*B25J 9/00* (2006.01)
*A61H 1/02* (2006.01)
*A61H 3/00* (2006.01)

(52) U.S. Cl.
CPC ..... *B25J 9/0006* (2013.01); *A61H 2201/1215* (2013.01); *A61H 2201/163* (2013.01); *A61H 2201/165* (2013.01); *A61H 2201/1642* (2013.01)

(58) Field of Classification Search
CPC .... A61H 2201/1215; A61H 2201/1642; A61H 1/00; A61H 1/02; A61H 1/0237; A61H 1/024; A61H 1/0244; A61H 1/0262; A61H 1/0266; A61H 2201/16; A61H 2201/1623; A61H 2201/1626; A61H 2201/1628; A61H 2201/164; A61H 2203/00; A61H 2203/04; A61H 2203/0406; B25J 9/0006; A61B 5/1038; A61B 5/4528; A61B 5/6829; A61B 2562/0219

See application file for complete search history.

(56) References Cited

U.S. PATENT DOCUMENTS

| | | |
|---|---|---|
| 2006/0260620 A1 | 11/2006 | Kazerooni et al. |
| 2007/0056592 A1* | 3/2007 | Angold .................... A61H 3/00 128/845 |
| 2011/0295164 A1* | 12/2011 | Jacobsen .................. A61F 2/68 601/23 |
| 2012/0271207 A1* | 10/2012 | Schoen ................. A61F 5/0102 601/34 |

* cited by examiner

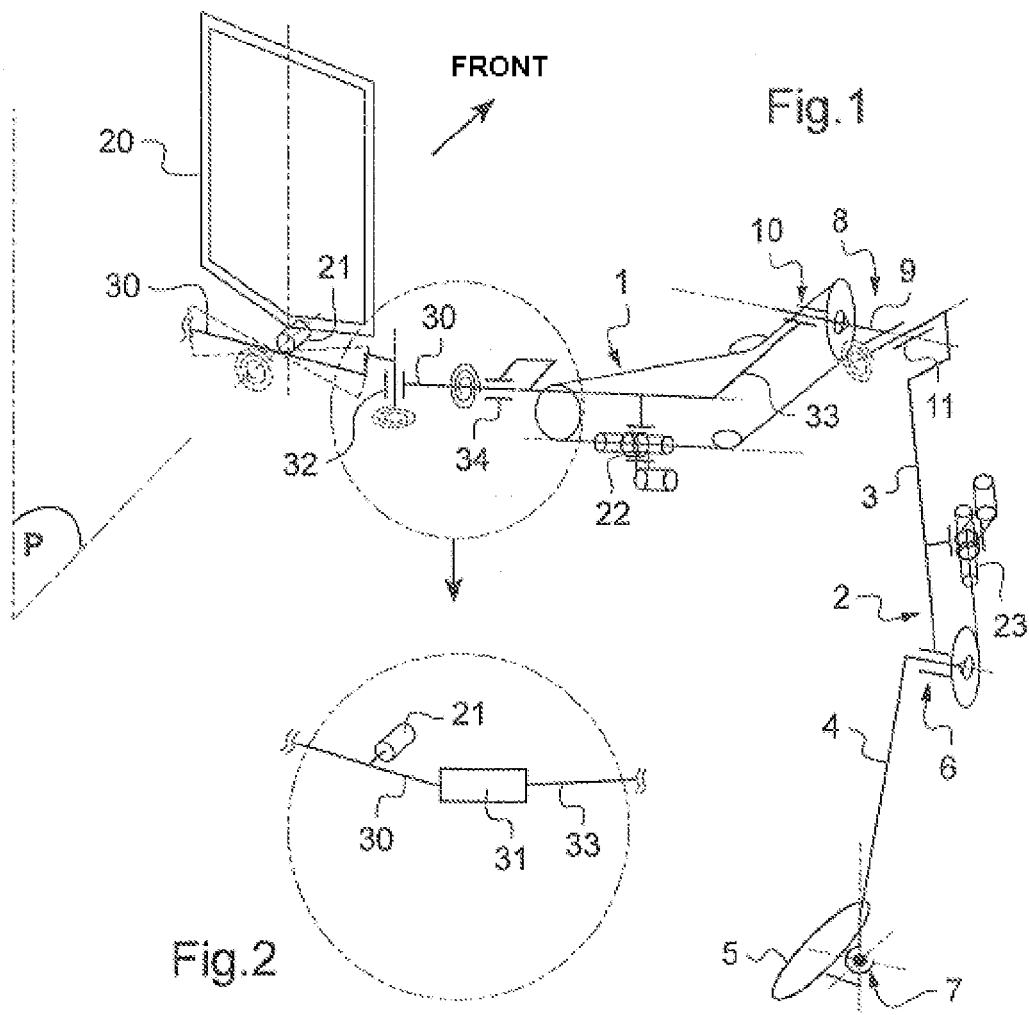
FRONT
Fig.1
Fig.2
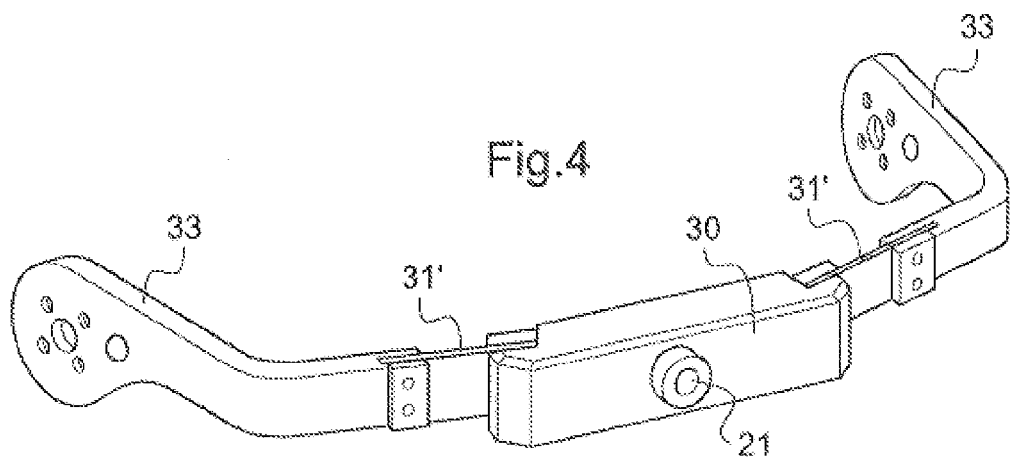
Fig.4

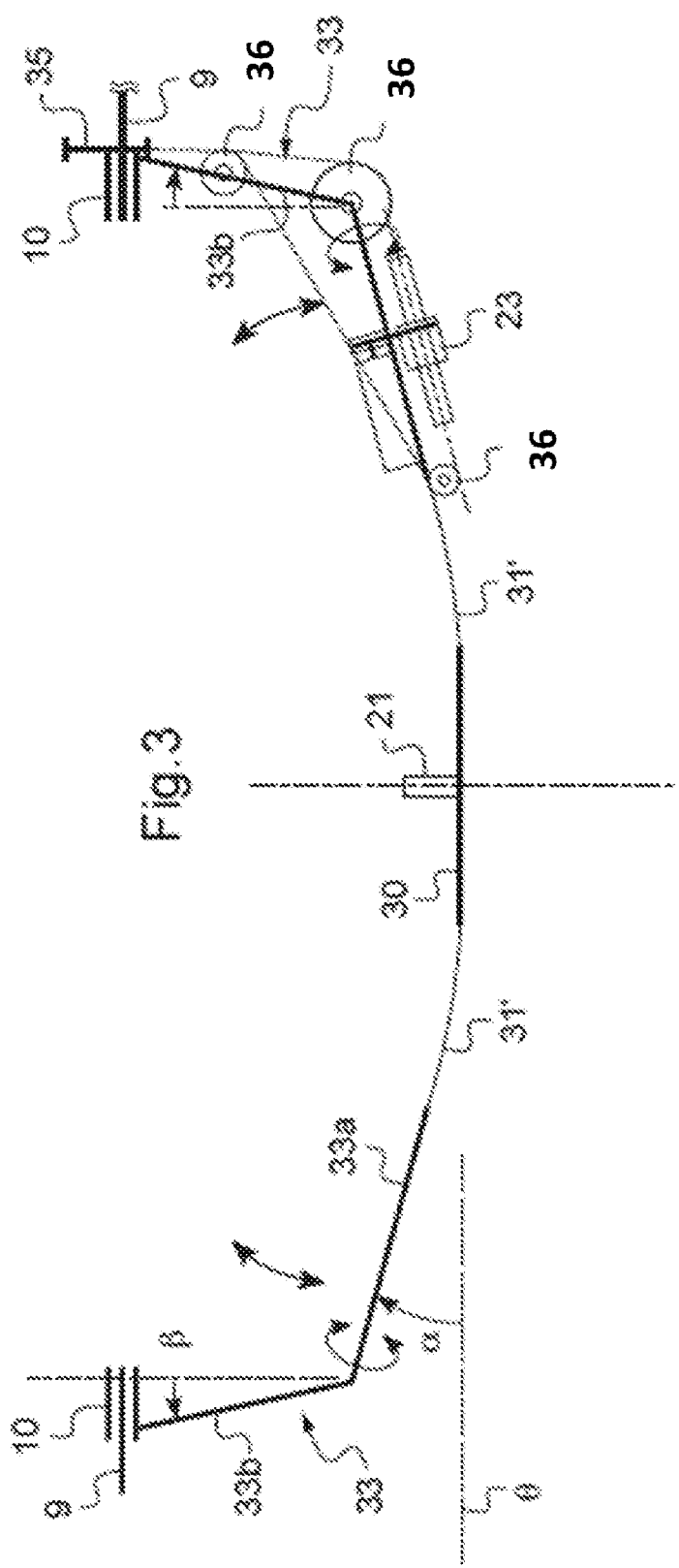

LOWER EXOSKELETON

The invention relates to an exoskeleton, more particularly a lower exoskeleton arranged in the area of the legs of the user.

In all of what follows, the stated orientations of the axes and planes are to be understood as being when the exoskeleton is worn by the user, with the lower limbs of the latter at rest.

BACKGROUND OF THE INVENTION

U.S. 2006/0260620 A1 discloses a lower exoskeleton intended to be worn by a user and having:
- a pelvic element provided with means for securing to an upper part of the body of the user;
- two lower supports which are provided with means for securing to the lower limbs of the user and which rest on the ground during the stance phases, each of the supports having a thigh segment and a tibia segment which are connected by a knee link configured to allow flexion and extension between the thigh segment and the tibia segment;
- hip links for connecting the two lower supports to the pelvic element.

In said document, the pelvic element is presented in a number of variants:
- in one part articulated along a longitudinal axis (horizontal axis contained in a sagittal plane) on a member for securing to the user (a belt, a dorsal support, etc.), in order to permit movements of abduction and adduction of the lower supports. It should be noted that, in this configuration, the abduction of one lower support necessarily causes the adduction of the other lower support;
- in two parts articulated along parallel longitudinal axes on a member for securing to the user, in order to permit independent movements of abduction and adduction of the lower supports;
- in two parts connected to the securing member by elastic hinges, in order to permit movements of abduction and adduction of the lower supports independently for each of the supports.

It has been found that pelvic elements of this kind do not always optimally follow the natural movements of the lower limbs of the user.

OBJECT OF THE INVENTION

The object of the invention is to make available a lower exoskeleton in which the thigh and leg segments more easily follow the natural movements of the lower limbs of the user.

SUMMARY OF THE INVENTION

In order to achieve this object, a lower exoskeleton is made available which is intended to be worn by a user and has:
- a pelvic element provided with means for securing to an upper part of the body of the user;
- two lower supports which are provided with means for securing to the lower limbs of the user and which rest on the ground during the stance phases, each of the supports having a thigh segment and a tibia segment which are connected by a knee link configured to allow flexion and extension between the thigh segment and the leg segment;
- hip links for connecting the two lower supports to the pelvic element.

According to the invention, the pelvic element has:
- an inner segment extending symmetrically in relation to a central sagittal plane and associated with the means for securing to the user;
- two outer segments extending symmetrically and being connected to respective distal ends of the inner segment by means of linking members, allowing at least flexion between the inner segment and each outer segment along two substantially orthogonal axes;
- each lower support being connected by one of the hip links to one of the outer segments.

Thus, the linking members interposed between the inner segment and the outer segments afford possibilities of deformation of the pelvic element, which allow the exoskeleton to better follow the natural movements of the lower limbs of the user.

According to a first embodiment of the invention, each linking member comprises an intermediate segment having a proximal end connected to a distal end of the inner segment by a pivot link along a vertical axis, and a distal end connected to a proximal end of the associated outer segment by a pivot link along a horizontal axis. The link thus constructed is akin to a cardan joint.

These pivot links will preferably be provided with adjusting members such as springs or dissipaters, or even with actuators if these links have to be controlled.

According to a second embodiment of the invention, each linking member comprises a deformable blade that extends along a substantially vertical plane and that has a proximal end engaged on a distal end of the inner segment, and a distal end engaged on a proximal end of the associated outer segment. The deformable blade can undergo flexion and torsion. The flexion of the blade ensures the flexion between the inner segment and each outer segment along a vertical axis, while the torsion of the blade ensures the flexion between the inner segment and each outer segment along a horizontal axis.

Of course, it will be possible for the inner segment to be broken down into two half-segments which are both connected to a member for securing to the user.

BRIEF DESCRIPTION OF THE FIGURES

The invention will be better understood on reading the following description of particular embodiments of the invention and by referring to the figures of the attached drawings, in which:

FIG. 1 is a schematic perspective view of a lower exoskeleton according to a first particular embodiment of the invention, only the right-hand part of the exoskeleton having been depicted, it being understood that the exoskeleton is symmetrical with respect to the central sagittal plane P;

FIG. 2 is a partial schematic view of the pelvic element of the exoskeleton of the invention, according to a second embodiment of the invention;

FIG. 3 is a schematic plan view of the pelvic element from FIG. 2;

FIG. 4 is a perspective view of an illustrative embodiment of the pelvic element from FIGS. 2 and 3.

DETAILED DESCRIPTION

Referring to FIG. 1, the lower exoskeleton of the invention is intended to be fitted on a user. To this end, it has a dorsal structure 20 intended to be fixed to the user's back, for example by means of a belt and straps. The exoskeleton has a pelvic element 1, which is here articulated at its center on the dorsal structure 20 via a pivot link 21 of longitudinal horizontal axis (that is to say a horizontal axis extending in a sagittal plane), and to which two lower supports 2 (only one is visible here) are connected, each of them having a thigh segment 3, a tibia segment 4, and a foot 5.

A knee link 6, here a pivot link of transverse horizontal axis (that is to say an axis perpendicular to the central sagittal plane P), connects the thigh segment 3 to the leg segment 4, while an ankle link 7, here a ball and socket, connects the tibia segment to the foot 5. Moreover, each thigh segment 3 is connected to the pelvic element 1 by a hip link 8, which has an intermediate linking member 9 connected, on the one hand, to the pelvic element 1 by a pivot link 10 of transverse horizontal axis and, on the other hand, to the thigh segment 3 by a pivot link 11 of longitudinal horizontal axis.

Of course, it will be possible for the knee, heel and hip links to be of any other configuration without this meaning that the exoskeleton is not covered by the scope of the invention.

Here, the pivot link 10 of the hip link 8 is associated with an actuator 22 in order to control a movement between the pelvic element 1 and the intermediate linking member 9. The actuator 22 here is a cabled actuator with a dual action. The way in which this actuator is installed on the pelvic element 1 will be returned to later. Moreover, the knee link 6 is associated with an actuator 23 arranged on the thigh segment 3 in order to control a movement between the tibia segment 4 and the thigh segment 3. The other pivot links here are equipped with springs for return to a position of equilibrium.

According to an essential aspect of the invention, the pelvic element is not in one piece but instead comprises:

an inner segment 30 directly articulated on the dorsal structure and symmetrical in relation to the central sagittal plane P, two intermediate segments 31 (only one is visible here) having a proximal end which is linked by a pivot link 32 of vertical axis to a distal end of the inner segment 30;

two outer segments 33 (only one is visible here) having a proximal end which, by means of a pivot link 34 of horizontal axis concurrent with the vertical axis of the pivot link 32, is linked to a distal end of one of the intermediate segments 31.

The pivot links 32 and 34 are here equipped with springs for return to a position of equilibrium.

The two freedoms thereby introduced allow the pelvic element to better follow the natural movements of the user. It will be noted that the intermediate segments 31 act in the manner of a cardan joint between the inner segment 30 and each outer segment 32.

As will be seen from FIGS. 2 to 4, in accordance with a variant of the invention, the rigid intermediate segments 31 are replaced by blades 31' which are deformable both in flexion and in torsion. Each of the blades 31' extends in a vertical plane and is engaged on a distal end of the inner segment 30 and on a proximal end of one of the outer segments 33. As is illustrated in FIG. 3 by arrows in thick lines, the blades 31' are elastically (or viscoelastically) deformable both in flexion and in torsion, such that the blades 31' allow the same movements of outer segments 33 vis-à-vis the inner segment 30 as in the preceding example.

According to a particular aspect of the invention, the outer segments 33 are bent, with a proximal end 33a extending substantially in the continuation of the associated distal end of the inner segment 30 and forming an angle α, preferably of between 5 and 30 degrees, with a coronal plane Q, and a distal end 33b extending to the front and forming an angle β, preferably of between −10 and +20 degrees, with a sagittal plane.

The cabled actuator 23 is here carried by the proximal end 33a of the outer segment 33 behind the pelvic element, and turn pulleys 36 allow the cable (shown by broken lines) to be returned to a pulley 35 rigidly connected to the intermediate linking member 9 of the hip link 9. Of course, although not shown, the other outer segment 33 also carries a cabled actuator.

Thus, the actuator for controlling the hip link is lodged on the user's back behind the pelvic element and can be easily integrated in the latter. The thigh segment is then free of an actuator, which contributes to reducing the lateral extent of the lower exoskeleton of the invention.

The invention is not limited to what has just been described and instead encompasses any variant falling within the scope of the invention as defined by the claims. In particular, although the inner segment of the pelvic element is in one piece in the example illustrated, it will of course be possible to use an inner segment in two parts, following the example of document U.S. 2006/0260620 A1. Although here the axes of intermediate flexion of the pelvic elements illustrated extend along concurrent vertical and horizontal directions (axes of the pivot links 32 and 34, axes of flexion and torsion of the blade 31'), the invention applies more generally to a pelvic element of which the outer segments are connected to the inner segment by linking members allowing flexion along two orthogonal axes, which may or may not be concurrent.

The invention claimed is:

1. A lower exoskeleton intended to be worn by a user and having:

a pelvic element provided with means for securing to an upper part of a body of the user;

two lower supports which are provided with means for securing to lower limbs of the user and which rest on a supporting ground during stance phases, each of the supports having a thigh segment and a tibia segment which are connected by a knee link configured to allow flexion and extension between the thigh segment and the tibia segment;

hip links for connecting the two lower supports to the pelvic element;

wherein the pelvic element has:

an inner segment extending symmetrically in relation to a central sagittal plane and associated with the means for securing to the upper part of the body of the user;

two outer segments extending symmetrically in relation to the central sagittal plane and being connected to respective distal ends of the inner segment by linking members, allowing at least flexion between the inner segment and each outer segment, respectively, along two axes orthogonal to one another;

each lower support being connected by one of the hip links to one of the outer segments;

wherein at least one hip link is operably associated with a cabled actuator.

2. The lower exoskeleton as claimed in claim 1, in which each linking member comprises an intermediate segment having a proximal end connected to a distal end of the inner segment by a pivot link along a substantially vertical axis relative to the user in a stance position, and a distal end connected to a proximal end of the associated outer segment by a pivot link along a substantially horizontal axis relative to the user in the stance position.

3. The lower exoskeleton as claimed in claim 2, in which the axes of the pivot links are concurrent.

4. The lower exoskeleton as claimed in claim 1, in which each linking member comprises a blade that is deformable in flexion and in torsion and that extends along a substantially vertical plane and has a proximal end engaged on a distal end of the inner segment, and a distal end engaged on a proximal end of the associated outer segment.

5. The lower exoskeleton as claimed in claim 2, in which each hip link has at least one pivot link controlled by an actuator arranged on the pelvic element.

6. The lower exoskeleton as claimed in claim 5, in which the actuator is rigidly connected to the outer segment carrying the hip link.

7. The lower exoskeleton as claimed in claim 6, in which the outer segment is bent, the actuator being carried by a proximal part of the outer segment connected to the inner segment.

8. A lower exoskeleton adapted to be worn by a user comprising:
  a pelvic element adapted to be secured to an upper part of a body of the user;
  two lower supports adapted to be secured to respective lower limbs of the user and that rest on a supporting ground during a standing position of the user, each of the two lower supports has a thigh segment and a tibia segment that are connected by a knee link configured to allow flexion and extension between the thigh segment and the tibia segment;
  hip links respectively connecting the two lower supports to the pelvic element;
  wherein the pelvic element comprises:
  an inner segment with two elongated portions extending symmetrically outward from a central sagittal plane towards respective distal ends of the inner segment so that the two elongated portions are symmetrical with respect to the central sagittal plane, the inner segment having a central connection to a mechanism for securing to the user;
  two outer segments extending symmetrically in relation to the central sagittal plane and connected to the respective distal ends of the inner segment by links, allowing at least flexion between the inner segment and each corresponding outer segment along respective two axes orthogonal to one another;
  each lower support connected by one of the hip links to one of the outer segments; and
  wherein at least one hip link is operably associated with a cabled actuator.

* * * * *